US012741105B2

(12) United States Patent
Young et al.

(10) Patent No.: US 12,741,105 B2
(45) Date of Patent: Sep. 22, 2026

(54) SURFACE ACOUSTIC WAVE ATOMIZER WITH FLUID DIRECTION AND MIGRATION PREVENTION

(71) Applicant: Trudell Medical International Inc., London (CA)

(72) Inventors: Heather Young, London (CA); Nicholas Baxter, Lucan (CA); Andrew Dittmer, Woodstock (CA)

(73) Assignee: Trudell Medical International Inc., London (CA)

( * ) Notice: Subject to any disclaimer, the term of this patent is extended or adjusted under 35 U.S.C. 154(b) by 1077 days.

(21) Appl. No.: 17/520,120

(22) Filed: Nov. 5, 2021

(65) Prior Publication Data

US 2022/0233789 A1 Jul. 28, 2022

Related U.S. Application Data

(60) Provisional application No. 63/110,777, filed on Nov. 6, 2020.

(51) Int. Cl.
*A61M 11/00* (2006.01)
*A61M 16/14* (2006.01)
*B06B 1/06* (2006.01)

(52) U.S. Cl.
CPC .......... *A61M 11/005* (2013.01); *A61M 16/14* (2013.01); *B06B 1/0644* (2013.01); (Continued)

(58) Field of Classification Search
CPC ........ A61M 11/005; A61M 2205/0294; A61M 1/005; A61M 15/001; A61M 15/0085; B05B 17/607; B05B 17/0638; B05B 17/063; B05B 17/0646; B05B 17/0676; A24F 42/20
See application file for complete search history.

(56) References Cited

U.S. PATENT DOCUMENTS 7,516,714 B2 * 4/2009 Yamagata ................. B05B 5/00 118/301
8,480,010 B2 7/2013 Ishigami
(Continued)

FOREIGN PATENT DOCUMENTS

CA 3097177 A1 * 10/2019 ............. A24F 40/05
CN 1468152 A * 1/2004 ......... B05B 17/0623
(Continued)

OTHER PUBLICATIONS

Guillermic; Article: A PDMS-based broadband acoustic impedance matched material for underwater applications; (Year: 2018).*
(Continued)

*Primary Examiner* — Victoria Murphy
*Assistant Examiner* — Sydney Reyes Russell
(74) *Attorney, Agent, or Firm* — Crowell & Moring LLP

(57) ABSTRACT

A surface acoustic wave (SAW) atomizer system for use in providing a nebulized medicament to a patient is described. The system may include a SAW atomization engine with an atomization region on a substrate that is separated from the interdigitated transducers (IDTs) on the substrate by a fluid barrier that seals off liquid fed into the atomization region from the adjacent IDTs and electrical contacts driving the IDTs.

16 Claims, 10 Drawing Sheets

(52) U.S. Cl.
CPC ............... *A61M 2205/0294* (2013.01); *A61M 2205/3379* (2013.01); *B06B 2201/77* (2013.01)

(56) References Cited

U.S. PATENT DOCUMENTS

| | | | | |
|---|---|---|---|---|
| 8,573,060 | B2 * | 11/2013 | Huang | C02F 1/505 73/570.5 |
| 11,097,544 | B2 * | 8/2021 | Muramatsu | B01L 3/0268 |
| 11,376,375 | B2 * | 7/2022 | Hijlkema | A61M 15/0085 |
| 11,413,407 | B2 * | 8/2022 | Porter | A61M 16/0672 |
| 2005/0178847 | A1 * | 8/2005 | Power | A61M 15/0085 239/4 |
| 2010/0282247 | A1 * | 11/2010 | Kadrichu | A61M 15/0086 128/200.14 |
| 2011/0192914 | A1 * | 8/2011 | Ishigami | A61M 15/0085 239/102.2 |
| 2012/0167877 | A1 * | 7/2012 | Pumm | B05B 17/0646 128/200.14 |
| 2013/0079733 | A1 * | 3/2013 | Burt | B08B 3/12 239/102.1 |
| 2013/0193227 | A1 * | 8/2013 | Hirai | B41J 2/055 239/102.2 |
| 2014/0014103 | A1 * | 1/2014 | Smaldone | A61M 16/0465 128/203.12 |
| 2017/0178884 | A1 | 6/2017 | Murtazin | |
| 2017/0333644 | A1 * | 11/2017 | Reboud | B05B 17/0607 |
| 2019/0285196 | A1 * | 9/2019 | Giusti | B81C 1/0015 |
| 2020/0360957 | A1 * | 11/2020 | Sakuma | B05B 7/0012 |
| 2022/0401662 | A1 * | 12/2022 | Yeo | B05B 1/267 |

FOREIGN PATENT DOCUMENTS

| | | | | |
|---|---|---|---|---|
| CN | 106377821 A * | 2/2017 | A61M 11/005 |
| CN | 107083941 A * | 8/2017 | B05B 17/0607 |
| CN | 108379702 A * | 8/2018 | A61M 11/00 |
| EP | 2 500 106 B1 | 9/2017 | |
| JP | 2000176014 A * | 6/2000 | A61M 11/00 |
| JP | 2008104966 A * | 5/2008 | A24F 47/008 |
| JP | 2010-253347 A | 11/2010 | |
| JP | 2011-011102 A | 1/2011 | |
| JP | 4915567 B2 | 4/2012 | |
| JP | 2015013234 A * | 1/2015 | B05B 17/0607 |
| WO | WO-2004045690 A1 * | 6/2004 | A61M 15/00 |
| WO | WO-2009013951 A1 * | 1/2009 | B05B 17/0615 |
| WO | WO-2014097939 A1 * | 6/2014 | A61M 11/005 |
| WO | WO-2016179664 A1 * | 11/2016 | B06B 1/0644 |
| WO | WO 2021/062494 A1 | 4/2021 | |

OTHER PUBLICATIONS

EspaceNet Translation Du CN106377821 (Year: 2017).*

Bose; The role of acoustofluidics in targeted drug delivery; highlighted paragraph, p. 4 (Year: 2015).*

Olivares; Article: Sputtered SiO2 as low acoustic impedance material for Bragg mirror fabrication in BAW resonators; highlighted paragraph, p. 1 (Year: 2009).*

Onanko; Article Acoustic attenuation in silicon and silicon oxide (Year: 2008).*

PE2E Translation Cao CN_107083941_A_H (Year: 2017).*

PE2E Translation Cui CN_108379702_A_H (Year: 2018).*

PE2E Translation Arai CN_1468152_A_H (Year: 2004).*

PE2E Translation Onishi JP_2000176014_A_H (Year: 2000).*

PE2E Translation Miyazaki JP_2008104966_A_H (Year: 2008).*

PE2E Translation Nara JP_2015013234_A_H (Year: 2015).*

PE2E Translation Asai WO_2014097939_A1_H (Year: 2014).*

EspaceNet Translation Nuno WO-2009013951-A1 (Year: 2009).*

Huang Q; Article: Influence of Waterproof Films on the Atomization Behavior of Surface Acoustic Waves; highlighted paragraph, p. 1 and 2 (Year: 2019).*

International Search Report and Written Opinion for International Application No. PCT/IB2021/060278 mailed Dec. 29, 2021 (14 pages).

* cited by examiner

FIG. 10

| Material | Density [kg/m3] | Speed of Sound [m/s] | Acoustic Impedence [MRayl] | Gold Mismatch [((Z1-Z2)/(Z1+Z2))^2] | LiNbO3 Mismatch [((Z1-Z2)/(Z1+Z2))^2] | Water Mismatch [((Z1-Z2)/(Z1+Z2))^2] |
|---|---|---|---|---|---|---|
| Gold | 19300 | 3240 | 62.532000 | | 0.296339 | 0.908928 |
| LiNbO3 | 4647 | 3970 | 18.45 | 0.296339 | | 0.723024 |
| Water | 997 | 1497 | 1.49 | 0.908928 | 0.723024 | |
| Air | 1.29 | 343 | 0.000442 | 0.999972 | 0.999904 | 0.998815 |
| Polyurethane | 400 | 1900 | 0.760000 | 0.952545 | 0.847999 | 0.105753 |
| Polydimethylsiloxane (PDMS) | 965 | 1076 | 1.038340 | 0.935732 | 0.798221 | 0.032203 |
| Silicone | 1200 | 1485 | 1.782000 | 0.892240 | 0.678698 | 0.007816 |

SURFACE ACOUSTIC WAVE ATOMIZER WITH FLUID DIRECTION AND MIGRATION PREVENTION

CROSS-REFERENCE TO RELATED APPLICATIONS

This application claims the benefit of U.S. Provisional Patent Application No. 63/110,777, filed Nov. 6, 2020, the entirety of which is hereby incorporated by reference herein.

TECHNICAL FIELD

The present disclosure relates to atomizers for use in the distribution of a medicament and, more particularly, to atomizers utilizing surface acoustic wave (SAW) technology.

SUMMARY

According to one aspect, a surface acoustic wave atomizer system for use in atomizing a medicament for patient delivery is disclosed. The system may include an atomizer engine comprising a piezoelectric substrate and at least one set of interdigitated transducers (IDTs) positioned on a first side of the substrate. The atomizer engine may further include an atomization region positioned on the first side of the substrate adjacent to the IDTs and a top plate positioned over the first side of the substrate and enclosing a portion of the substrate other than the atomization region, such that the at least one set of IDTs are enclosed under the top plate. A fluid barrier surrounding the atomization region is further included on the substrate that forms a seal against the substrate and the top plate, where the fluid barrier is positioned to prevent liquid in the atomization region from coming into contact with the IDTs on the first side of the substrate.

In another aspect of the disclosure, a surface acoustic wave atomizer system for use in atomizing a medicament for patient delivery includes an atomizer engine. The atomizer includes a piezoelectric substrate having a first side and a second side. An atomization region is positioned on the first side of the substrate for receiving liquid to be atomized from a liquid supply, along with at least one transducer positioned on the substrate adjacent to the atomization region. The at least one transducer is electrically excitable to generate acoustic energy at a frequency and amplitude sufficient to atomize fluid received in the atomization region. Additionally, the atomizer engine includes a fluid barrier separating the atomization region on the substrate from the at least one transducer, where the fluid barrier is positioned to prevent fluid in the atomization region from coming into contact with the at least one transducer.

In yet another aspect, a surface acoustic wave atomizer system for atomizing a fluid for patient delivery is disclosed including a piezoelectric substrate having a side with at least one interdigitated transducer and an atomization region separate from the at least one interdigitated transducer. A top plate is spaced away from the side of the substrate and encloses the side of the substrate other than the atomization region, where the substrate is captured between the top plate and a base. A fluid barrier is attached to the top plate and surrounds the atomization region on the substrate, the fluid barrier defining an atomization path from the atomization region through the top plate and separating the at least one interdigitated transducer from the atomization region. A fluid supply channel is included that extends through a wall of the fluid barrier from a first fluid channel opening in a portion of the fluid barrier outside of the top plate to a fluid orifice in the fluid barrier oriented toward the atomizing region and between the outside of the top plate and the substrate. The fluid barrier is formed of a material highly acoustically mismatched with the substrate and the top plate, and highly acoustically matched with the fluid.

BRIEF DESCRIPTION OF THE DRAWINGS

FIG. 10 is a table of calculated material acoustic impedances and their mismatch to gold, lithium niobate and water.

DETAILED DESCRIPTION

Atomizers are devices that shear bulk fluid into discrete droplets for a variety of applications, such as medical nebulizers, fuel injectors, perfumes, cleaning products, etc. Because the natural state (the lowest energy state) of fluid is as a bulk, work must be done to break it down and it will always try to agglomerate. There are different ways to break up a fluid, in general the surface is disturbed to produce a thin column of fluid (jet), and when the conditions are right (Weber's #>1, i.e. fluid kinetic energy>> surface energy), the tip of the column is separated from the bulk of the fluid. For smaller droplets, satisfying the critical weber number becomes increasingly difficult as the mass of the fluid is proportional to the diameter cubed, while the surface energy is proportionally squared. In other words, the diameter affects the numerator more than the denominator, and so to keep the ratio above the critical value the kinetic energy must get respectively higher. For very thin columns of fluid, vibrations in the fluid help with break up, as harmonic perturbations will quickly grow and lead to contractions that eventually allow the tip of the fluid column to be pinched off (Rayleigh plateau instability).

The goal of any commercial atomizer is to efficiently provide aerosol droplets within a desired size range without damaging the contents of the fluid. An additional criterion exists for pressure sensitive systems (such as in a respiratory circuit), where deviation in pressure can be catastrophic. Solutions with minimal impact, i.e., those that deliver only the aerosol, are preferred because the displaced volume of the fluid is negligibly small with respect to the system volume and avoids the need for intervention (human or AI) to accommodate it. In some cases, controlling the rate of delivery is also pertinent, for certain medical applications the treatment time is seen as proportional to the monetary cost, but rate control can also be significant for balancing medication bioavailability, metabolism and side-effects.

There are multiple technologies that are commonly used to produce an aerosol: pneumatic (low velocity fluid and high velocity air), hydraulic (high velocity fluid and low velocity air), mesh (vibration or static), free surface (ultrasonic, Surface Acoustic Wave (SAW)), spinning (centrifugal), electrostatic, and Fourier horn.

Medical nebulizers are a specific application of an atomizing device that nebulize a fluid into an aerosol for inhalation by a patient. Medical nebulizers are well-known devices commonly used for the treatment of certain conditions and diseases. Nebulizers have applications for conscious, spontaneously-breathing patients and for controlled, ventilated patients.

Figure 1:
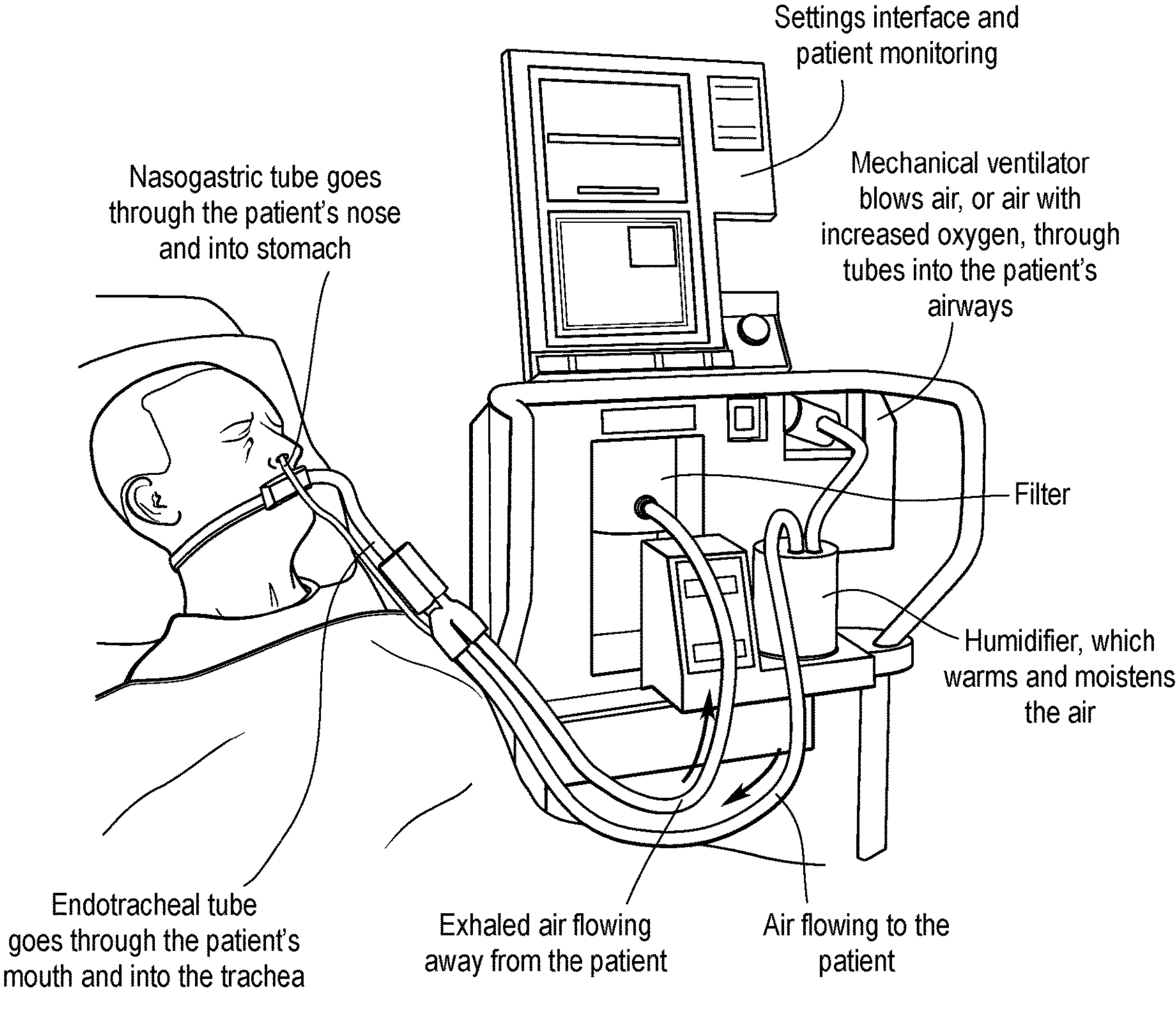
FIG. 1 is an example of a pressure sensitive system of a typical ventilator circuit.

Patients who suffer serious respiratory distress due to infection or other causes can require assistance with breathing in the form of mechanical ventilation. A ventilator device is connected to the patient's airway and performs the work of breathing on behalf of the patient so that their lungs can recover from whatever condition they are afflicted with. A typical ventilator circuit 3 is described in FIG. 1.

Aerosol therapy is currently delivered to mechanically ventilated patients by various means. The most common are either with a pressurized metered dose inhaler (MDI) or a nebulizer. MDI's deliver a high concentration dose in single "metered" doses and are delivered to mechanically ventilated patients via some form of adapter that receives the MDI and allows it to introduce the dose of aerosol to the breathing circuit. Metered dose inhalers are drug specific and so if different drugs are to be administered to a patient, a unique MDI must be used for each drug. MDI's contain a mixture of drug and propellant in a canister that when actuated through a metering valve, is driven through a small orifice under high pressure. During release of the medication and propellant through the orifice, rapid expansion and evaporation of the propellant occurs causing the liquid medication to form aerosol droplets. While MDI's are very common and available for most medications, they are customized to each drug formulation and so a unique MDI must be used for each medication a patient requires. In hospital settings, infection prevention protocols often lead to leftover drugs being discarded, adding significant cost to the system.

In comparison, nebulizers can deliver many types of aerosol medication. Nebulizers used in delivering aerosol to mechanically ventilated patients fall into two categories described as jet nebulizers and mesh nebulizers. Jet nebulizers are connected by tubing to a supply of compressed gas, usually compressed air and/or oxygen which flows through a small orifice to create a Venturi effect. This causes the liquid medication contained within the nebulizer to turn into an aerosol that is inhaled by the patient. Jet nebulizers are a well-established technology. They are very low cost but have one key disadvantage when compared to MDI's and mesh nebulizers and that is that they introduce a significant amount of added air flow to the ventilator circuit 3. This is a result of the driving gases required to operate the nebulizer which are introduced to the closed breathing circuit during aerosol delivery. This added flow must be carefully compensated for via adjustments to settings on the ventilator so that harm to the patient is prevented. Mesh nebulizers on the other hand do not introduce any additional flow to the circuit as the energy required to create the aerosol is generated via electromechanical energy communicated to the medication via a piezoelectric element. The vibrations cause the mesh plate in contact with the medication to vibrate which forces the liquid medication through micro-orifices machined in the mesh plate creating the aerosol. A disadvantage with mesh nebulizers is that the micro-orifices are fixed in dimensions which limits its application to medications that have different characteristics including viscosity and to those formulations that are suspensions containing both liquid and solid particles. The varying fluid characteristics can have a negative impact on key aerosol characteristics including aerosol particle size diameter and output rate of the nebulizer. Additionally, due to the small size of the micro-orifices, clogging is a commonly known challenge whereby drug residues, or solid particles in suspension formulations, can block the orifices and degrade performance.

A third technology to be described here uses surface acoustic wave (SAW) technology. SAW nebulizers operate on a principle of introducing high frequency vibrations into a crystalline substrate whereby liquid medication is delivered to the surface of the vibrating substrate. Energy transfer occurs at the liquid-surface interface and is sufficient to shear the liquid medication into aerosol particles. While SAW technology has been in existence for some time, as applied to nebulization it has been a challenge to provide a cost-effective solution while achieving the required aerosol quality and output rate necessary to be suitable for general purpose nebulizer treatment. Other challenges exist, including how to properly control the delivery of the liquid medication to the surface of the substrate, how to ensure durability and control safety risks posed by the fragile crystal, how to attain an efficient and effective aerosol particle size distribution, how to effectively contain fluid despite the high power required to atomize, and how to achieve an acceptable level of efficiency which also relates to problems with heat generation.

SAW technology is widely used in many industries but in the application of atomization there are unique challenges which must be overcome and are not evident in the prior art:

1) Some fluids being atomized are electrically conductive. This means that control of the fluid on the surface of the substrate is required to not only ensure it is accurately delivered to the atomization region, but so that it does not migrate to areas where the properties of the fluid can cause issues. Notably, liquid medication in the area of the interdigitated transducers 19 (IDTs) can cause numerous problems including electrical shorting or arcing across IDTs, resulting in physical damage, due to its electrical conducting properties.
2) Physical damage can occur due to the energy transfer between the fluid and the metal surfaces of the substrate. Degradation in the form of ablation of the metalized surfaces of the substrate can occur which, in excess, will cause degradation to device performance. While containment of fluids in medical devices is not a unique challenge, what is unique to a SAW nebulizer is to solve this problem without unduly affecting the acoustic properties and therefore performance of the SAW nebulizer. Preferably, a physical barrier is introduced that isolates and contains the medication to the atomization region 11 only and prevents it from contacting the IDTs located adjacent to the atomization region 11. The challenge with any physical barrier that comes into contact with the surface of the substrate is to prevent alteration of the acoustic behavior and resonance of the substrate.

3) Fluid trapped between the substrate and another component of the device causes dampening and loss of energy in the system, negatively impacting f device performance.

EXAMPLE EMBODIMENTS

In the examples below, the part numbers associated with the figures are found in Table A below:

TABLE A

Table of Element Numbers and Names

| Element No. | Element Name |
|---|---|
| 1 | Atomizer |
| 2 | Controller |
| 3 | Ventilator Circuit |
| 4 | Ventilator Adapter |
| 5 | Fluid Reservoir |
| 6 | Fluid Fill Port |
| 7 | Fluid |
| 8 | Pump |
| 9 | Fluid Delivery Channel |
| 10 | Electrical Connector |
| 11 | Atomization Region |
| 12 | Atomizer Engine |
| 13 | Gas Pathway Fitting |
| 14 | Atomized Fluid |
| 15 | Electrical I/O |
| 16 | Atomization chamber |
| 17 | Fluid Barrier |
| 18 | Substrate |
| 19 | Interdigitated Transducer (IDT) |
| 20 | Fluid Deliver Micro-Channel |
| 21 | Electrical Contact |
| 22 | Bonding Layer |
| 23 | Base |
| 24 | Top Plate |
| 25 | Printed Circuit Board (PCB) |
| 26 | Pressure equalizing channel |
| 27 | Fluid Micro Orifice |
| 28 | Air Cavity |
| 29 | Air flow from Air Cavity to Atomization Area |
| 30 | Left Side Positive Electrical Contact |
| 31 | Left Side Negative Electrical Contact |
| 32 | Right Side Positive Electrical Contact |
| 33 | Right Side Negative Electrical Contact |
| 34 | Clearance between Fluid Barrier and Substrate |
| 35 | Combined Controller and Atomizer with Mask |
| 36 | Combined Controller and Atomizer with Mouthpiece |
| 37 | Smart Phone, Tablet, or Computer |

Figure 2:
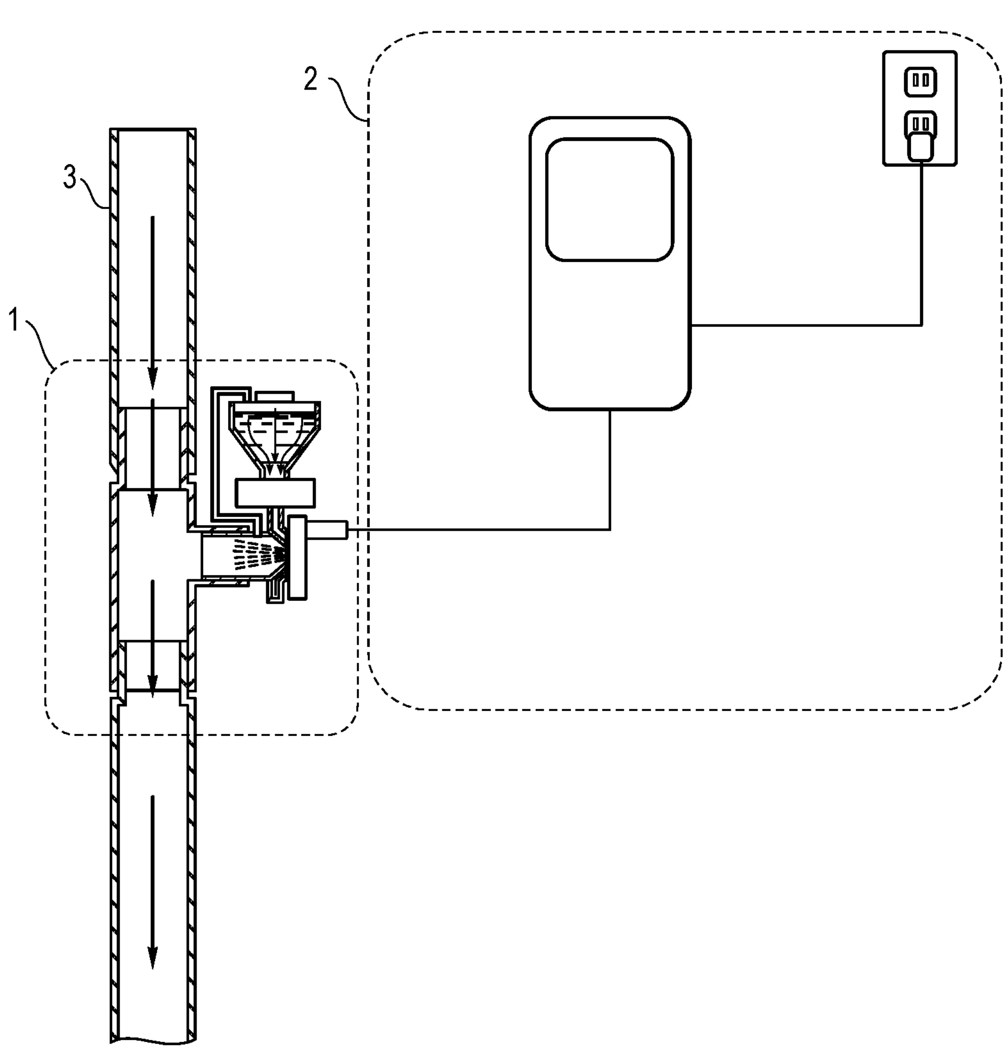
FIG. 2 illustrates a surface acoustic wave (SAW) atomizer system in a ventilator circuit according to one embodiment.
Figure 3:
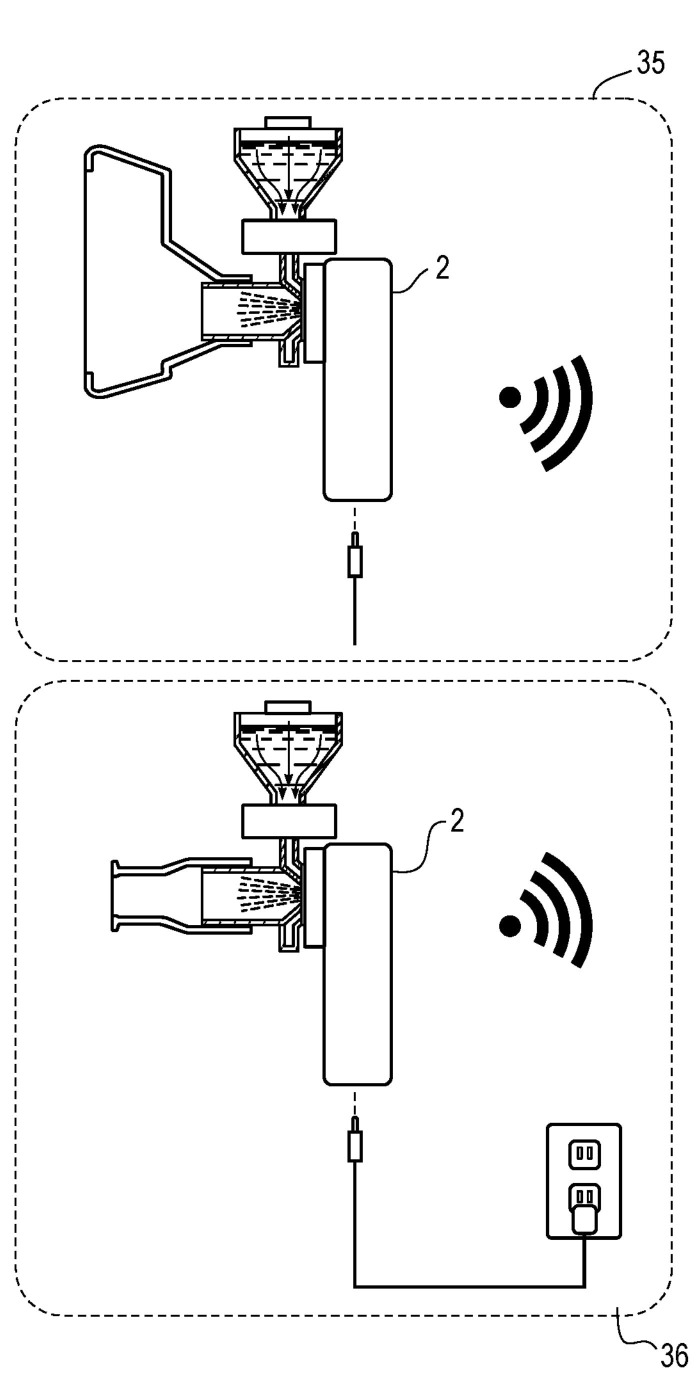
FIG. 3 illustrates a SAW atomizer system in a handheld configuration with smart phone communication.
Figure 3:
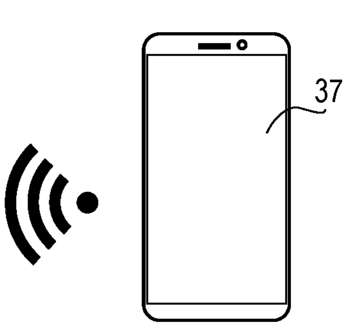

In order to address some of the challenges noted above, some non-limiting examples of SAW nebulizer (atomizer) designs are described below. Referring to FIG. 2, in one embodiment, the atomizer system is applied to a mechanically ventilated patient. The system is designed such that the atomizer system is comprised of two subsystems. The first subsystem forms the atomizer 1 of the device that contacts directly the medication being delivered and the ventilator circuit 3, including breathing gasses and fluids. The second subsystem forms the controller 2 portion of the device which forms the primary user interface whereby the device is operated. The controller 2 will include the power source for the atomizer 1 which may be in the form of a power cable connected to an outlet, a battery, or a combination. The controller 2 will connect to the atomizer 1 via an I/O cable to communicate electrical signals. Alternately, and not shown in the drawings, the atomizer 1 may combine elements of the controller 2 portion or be one system. In particular, for handheld operation for spontaneously breathing patients all controls and power sources would be integrated, as illustrated in FIG. 3. This atomizer can be configured with a mouthpiece 35 or mask 36 to deliver medication to a spontaneously breathing patient. In addition, communication with the controller 2 portion may be through a physical user interface directly on the controller 2 or remotely via a wireless communication and an alternate user interface, possibly via an application running on a smart phone 37, watch, or computer. As an alternative implementation, the power source for the atomizer 1 may be connected directly to the atomizer 1 where communication signals from the controller 2 are delivered wirelessly, via BLUETOOTH™, Wi-Fi, or some other form of wireless communications protocol as illustrated in FIG. 3.

In one embodiment, the atomizer 1 is configured to connect to a ventilator adapter 4 suitably configured to connect to a ventilator circuit 3 and position the atomizer 1 in an optimized orientation to deliver the atomized fluid 7 medication. The atomizer 1 is preferably connected to the adapter via a standard fitting 13 that allows the atomizer 1 to be removed and replaced while maintaining an effective seal with the ventilator adapter 4 when installed.

Figure 4:
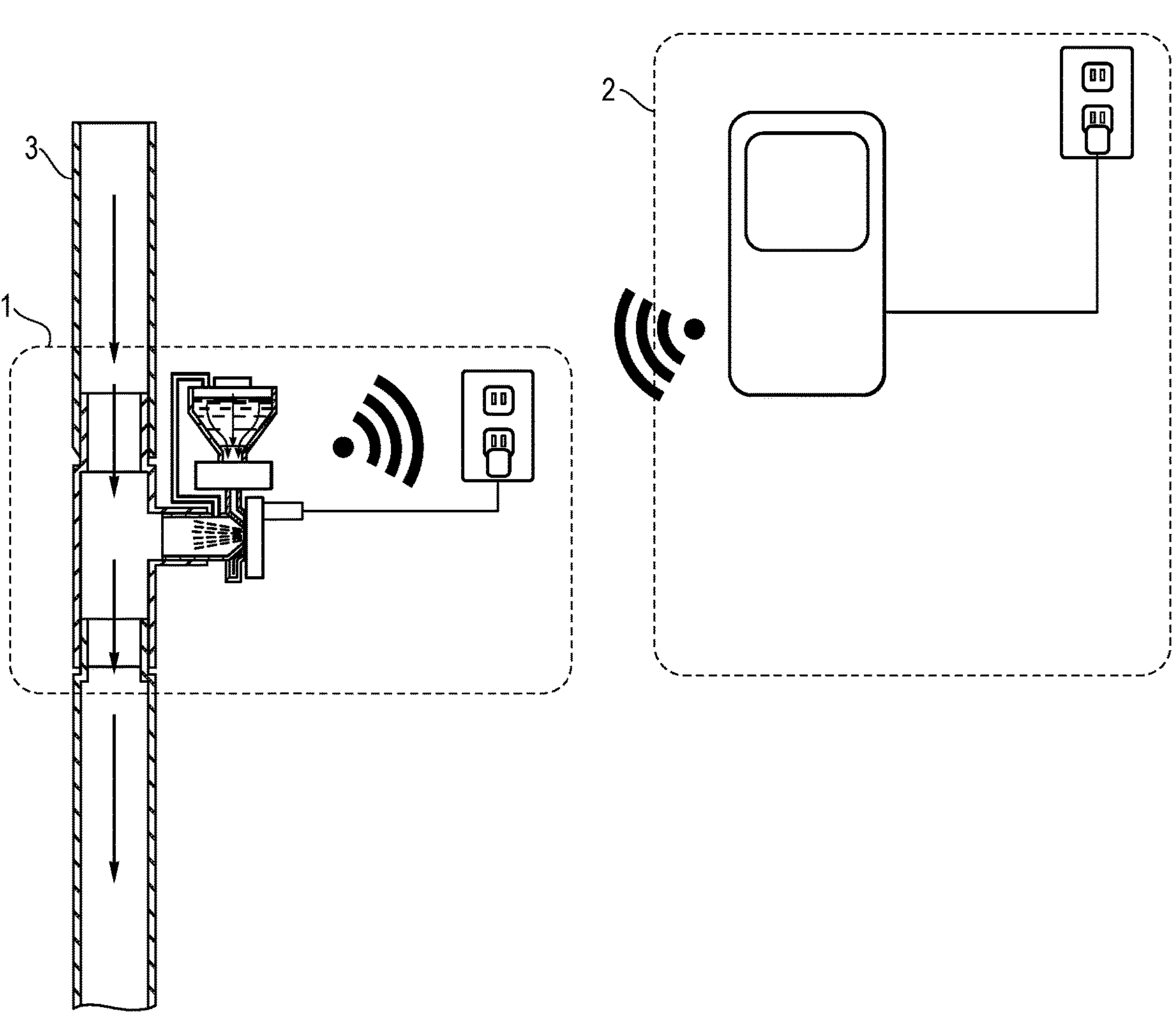
FIG. 4 is an alternative embodiment of the system of FIG. 2.

While the atomizer 1, as described in FIGS. 2 and 4, interfaces with a mechanical ventilator circuit 3, alternate embodiments can be designed such that the atomizer 1 can also connect to other forms of interfaces that would allow the atomized fluid 7 medication to be delivered to different types of patients and in different settings. This includes face masks, nasal masks, mouthpieces, nasal cannula and other forms of delivery methods suitable for spontaneously breathing patients or patients that may require non-invasive ventilatory support (See, e.g., FIG. 3).

Referring now to FIG. 4, the atomizer 1 in one embodiment is made up of the following elements. A reservoir contains the liquid medication and positions it at the inlet of the pump 8 to be delivered to the atomizer engine 12. The fluid reservoir 5 is sufficiently sized to accommodate an amount of liquid medication to facilitate treatment and with different forms of medication. A fill port 6 is positioned at the top of the fluid reservoir 5 to allow the liquid medication to be added to the fluid reservoir 5. The fill port 6 is preferably designed to close and seal the reservoir from the ambient conditions. The fill port 6 is also preferably configured to adapt to an outside fluid delivery source to enable continuous delivery of liquid medication amounts in excess of the capacity of the fluid reservoir 5. A pump 8 is configured between the fluid reservoir 5 and the atomizer engine 12 in order to both deliver the fluid 7 to the atomizer engine 12 but also to do so at the correct flow rate for optimal delivery. The pump 8 is configured to deliver fluid 7 to the atomizer engine 12 via a fluid delivery channel 9 which may be integrated into a number of different components of the atomizer 1. Importantly, the fluid delivery channel 9, or channels in the case where multiple are advantageous, must interface with the atomizer engine 12 so that the fluid 7 may be delivered to the atomization region 11 in the optimal location and at the optimal flow rate. The atomizer engine 12 is suitably connected to the atomization chamber 16. A pressure equalizing channel 26 is connected between the upper portion fluid reservoir 5 and the atomization chamber 16 which is exposed to the environment within the ventilator. The pressure equalization channel 26 ensures that there is no pressure differential between the fluid reservoir 5 and the atomization region 11 which may affect fluid delivery. An electrical connector 10 connects the atomizer 1 to the controller 2 so that appropriate electrical control signals are communicated to operate the atomizer 1.

The atomizer 1 includes a crystal or piezoelectric substrate, preferably lithium niobate, with one or more sets of interdigitated transducers 19 (IDTs) to generate a surface acoustic wave. These IDTs can take on standard or more specialized forms such as SPUDT, DART, fSAW, chirped, etc., and other potential substrate materials include quartz, lithium tantalate, etc. The acoustic wave energy is used to excite the medication in the atomization region 11 of the substrate to form aerosol particles. The substrate may be made up of a single crystal SAW material such as lithium niobate, lithium tantalate or quartz. Several parameters are considered when selecting a substrate material for a surface acoustic wave device. A material with a high electromechanical coupling coefficient ($K^2$) is desired. This coupling factor is the conversion efficiency between the electrical input and the acoustic or mechanical energy in the piezoelectric materials. The coupling coefficient, $K^2$, is preferably greater than 2% and most preferably greater than 5%. In one embodiment a preferred $K^2$ range of 2%-15% may be used, where $K^2$ above 15% would also be suitable but would depend on other characteristics as well. Lithium niobate is one preferred substrate material due to its relatively high $K^2$ (approximately 5.5%) compared to some other single crystal materials. A downside of lithium niobate is the temperature stability and the inherent pyroelectricity of the material. Pyroelectricity is an electrical response or ability to create a voltage when exposed to a change in temperature. This has negative effects in both processing of the substrate when developing the metallized IDT structures, as well as during operation. Black lithium niobate is preferred over standard lithium niobate as the black material has the ability to neutralize these electrical charges, while maintaining all other piezoelectric properties of the standard material.

Figure 5:
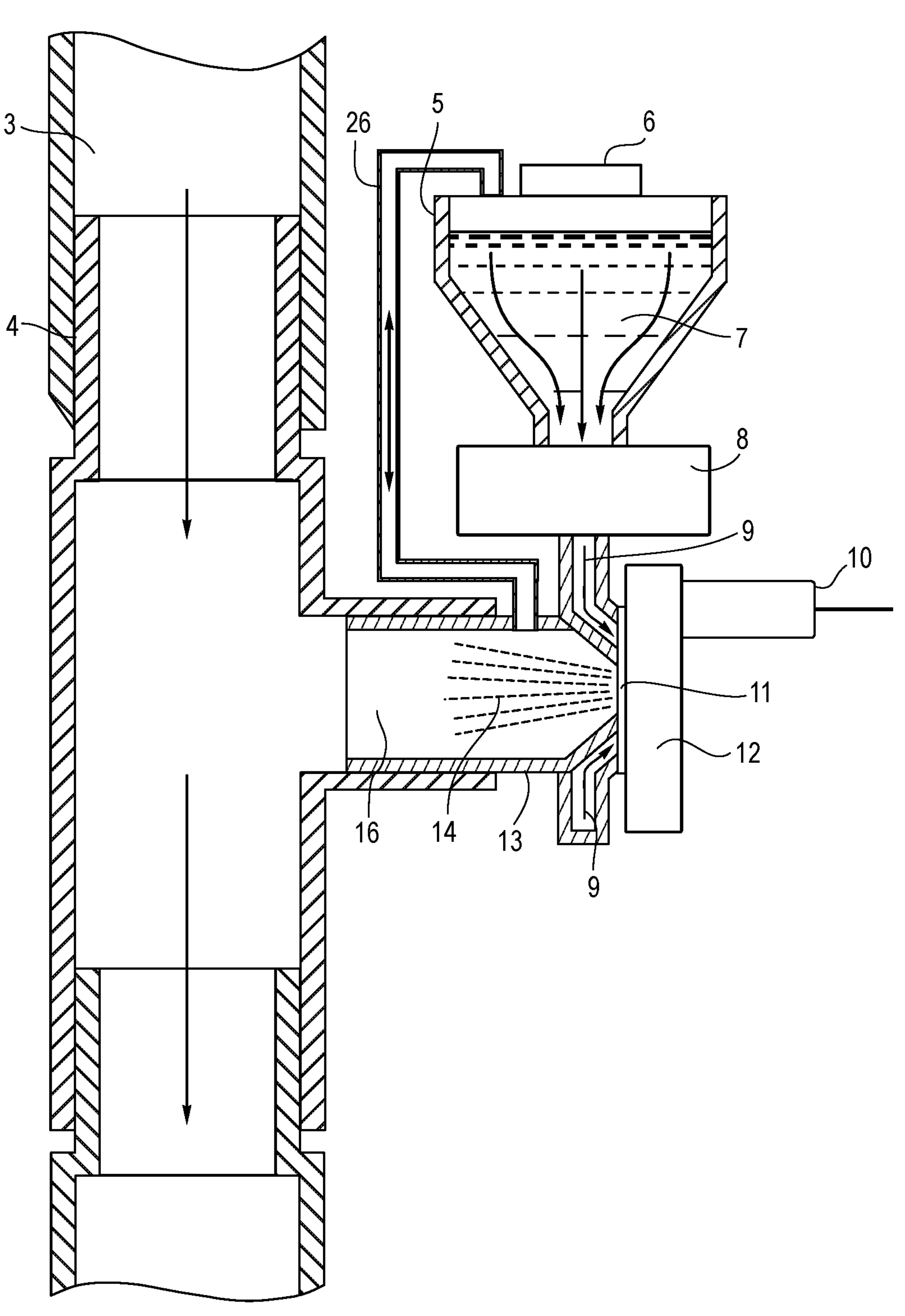
FIG. 5 is an expanded view of a portion of the SAW atomizer system illustrated in FIGS. 2-4.
Figure 6A:
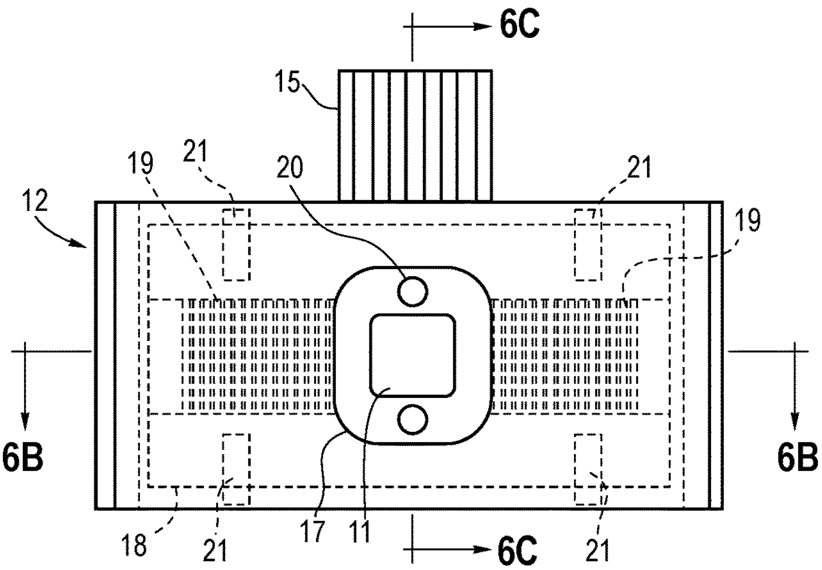
FIG. 6A is a top view of an embodiment of an atomizer engine that may be used in the system of FIGS. 2-5.
Figure 6B:
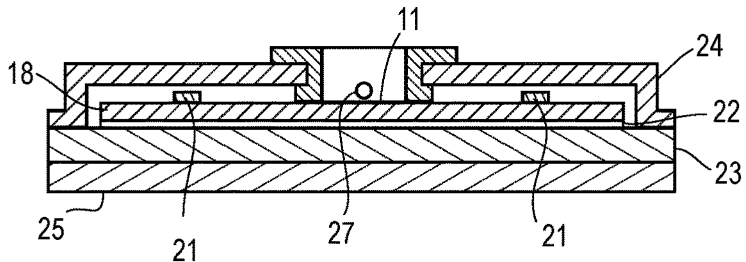
FIG. 6B is a side sectional view taken along line B-B of FIG. 6A.
Figure 6C:
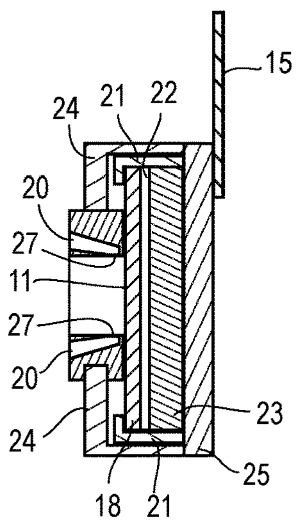
FIG. 6C is a side sectional view taken along line C-C of FIG. 6A.
Figure 7:
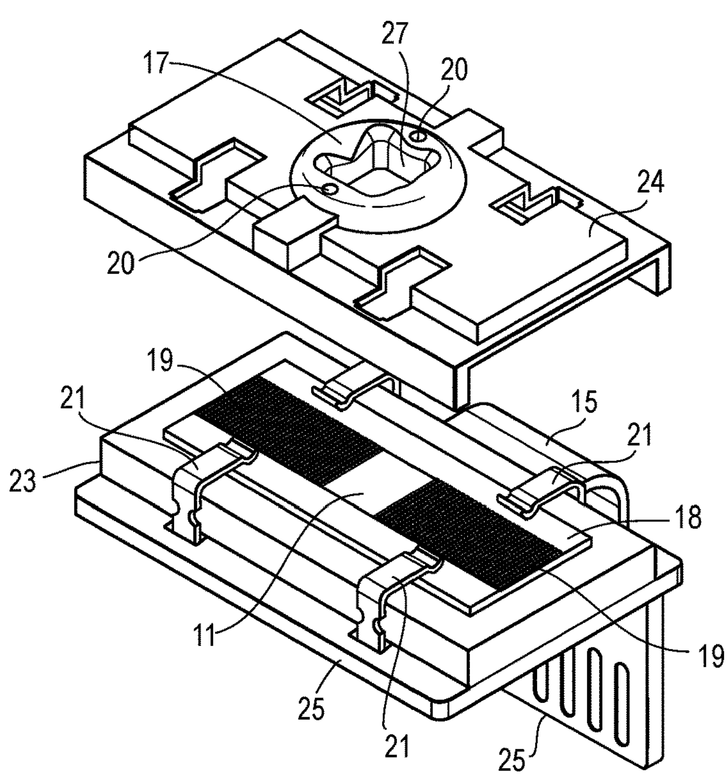
FIG. 7 is an exploded view of the atomizer engine of FIG. 6.

The atomizer engine 12 is described with reference to FIGS. 5-7. The atomizer engine 12 includes a crystal or piezoelectric substrate, preferably lithium niobate, with one or more sets of IDTs 19 to generate a surface acoustic wave. The IDTs 19 are formed of metal, preferably titanium, gold or some combination thereof. Alternate materials, including aluminum and chromium are also considered. A base 23, preferably rigid and formed of metal, metal alloy, or ceramic material which has advantages for heat conduction robustness, and safety. A bonding layer 22 that permanently and robustly bonds the crystal substrate 18 to the base 23 and is in the form of adhesive, for example silicone, that has a low attenuation property. The bonding layer 22 has excellent thermal conduction properties but also acts as an insulator electrically. A printed circuit board 25 (PCB) to which the base 23 is mounted where the PCB 25 has some form of connection that enables electrical signals to be delivered to the atomizer 1 from the controller 2. Electrical contacts 21 are formed between the PCB 25 and the IDTs 19 on the surface of the piezoelectric substrate for inputting the electrical signal to the substrate to generate an acoustic wave for manipulation of the medication, where the electrical contacts 21 are integrated and contact the top surface of the crystal substrate 18. A top plate 24 which encloses some or all of the crystal substrate 18, IDTs 19, bonding layer 22, base 23, electrical contacts 21, and some or all of the PCB 25. The top plate 24 is of a rigid material, preferably steel, ceramic or another metal, and houses the fluid barrier 17.

A solution is proposed for forming a fluid barrier 17 that effectively seals off the atomization region 11 on the surface of the substrate from the rest of the substrate, including IDTs 19 and electrical contacts 21, and also seals against the top plate. The fluid barrier 17 is positioned between the crystal substrate 18 and the top plate with sufficient contact area and pressure to form a seal at both interfaces. The fluid barrier 17 may also be physically or chemically bonded to the top plate 24 but is preferably removably attached to the surface of the substrate with a compressive preload. Combined they provide a physical barrier that prevents liquid from entering a protected region where the IDTs 19 and electrical contacts 21 are located as well as forming a suitable interface with both the moist environment of the ventilator circuit 3 and the fluid delivery channel 9 to the atomization region 11 of the substrate.

Figure 8:
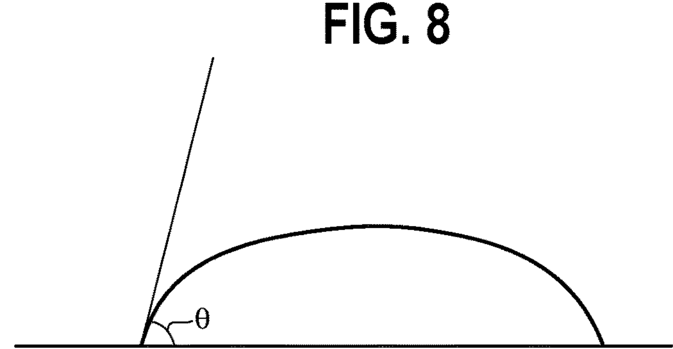
FIG. 8 illustrates a contact angle of a drop of liquid with a solid surface.
Figure 9:
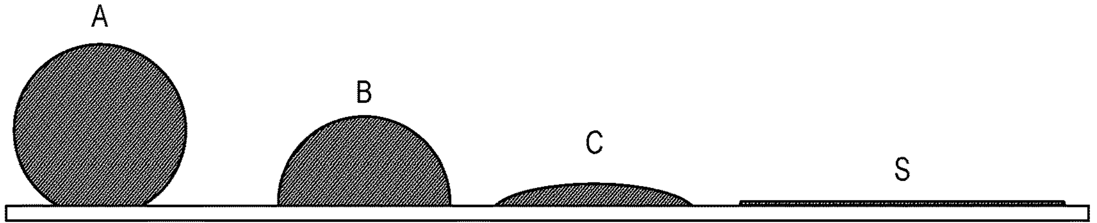
FIG. 9 illustrates wettability of a solid surface as shown through different. example contact angles of a liquid on the solid surface.
Figure 11:
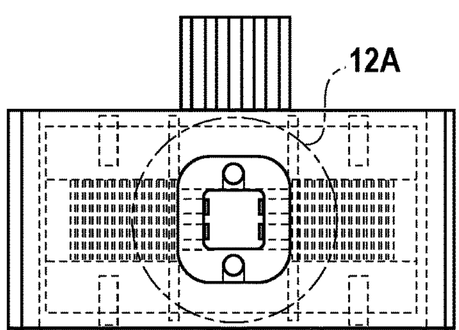
FIG. 11 is a top view of an alternative embodiment of the atomizer engine of FIG. 6A.
Figure 12A:
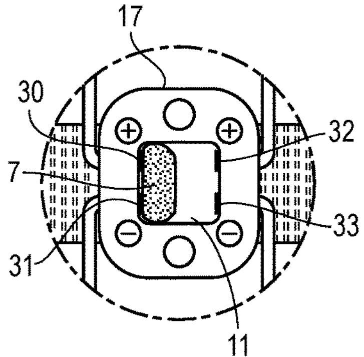
FIGS. 12A-12C are top sectional views of the atomizer engine of FIG. 11 illustrating a fluid located at different positions of the atomization region.
Figure 12B:
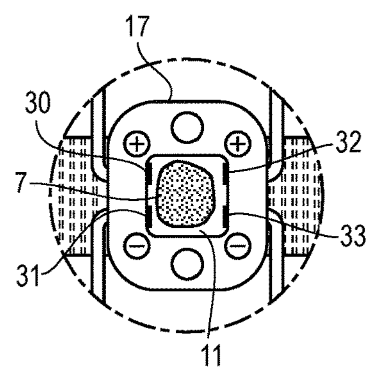
Figure 12C:
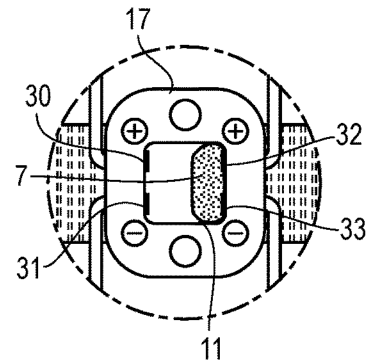
Figure 13:
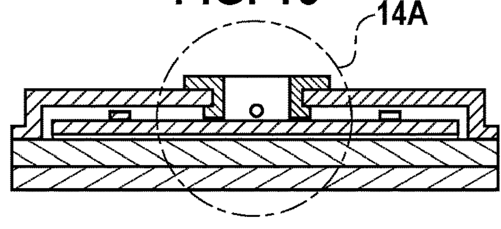
FIG. 13 is a side sectional view taken along line A-A of FIG. 11.
Figure 14A:
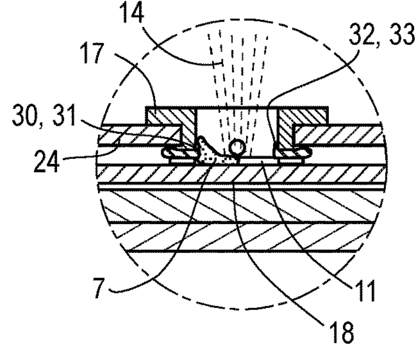
FIGS. 14A-14C are side sectional views of the atomizer engine of FIG. 13 illustrating a fluid located at different positions of the atomization region.
Figure 14B:
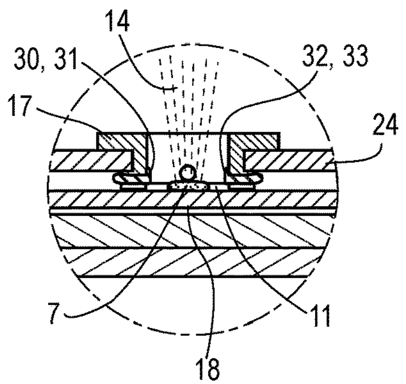
Figure 14C:
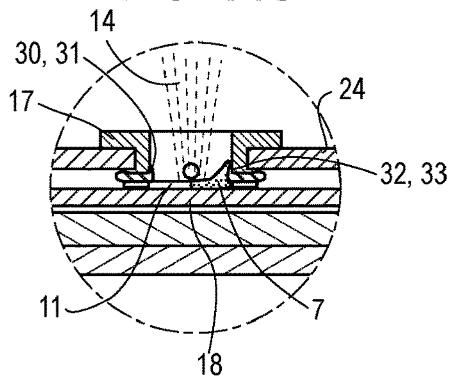

Operation of the SAW nebulizer may be achieved in any orientation, including the atomization region 11 facing downward, in different embodiments. In one embodiment, the fluid barrier 17 is designed to accommodate the orientation flexibility of the device and effectively seal off the protected area of the IDTs 19 and electrical contacts from the fluid present in the atomization region 11 in any orientation. In other embodiments, the SAW nebulizer may include an atomizing region 11 of high wettability to allow the device to operate in any orientation, including facing downward. As used herein, wettability relates to the adhesion of a liquid to a solid surface. Adhesive forces between a liquid and solid cause a liquid drop to spread across the surface. Cohesive forces within the liquid cause the drop to ball up and avoid contact with the surface. The contact angle is the angle at which the liquid—vapor interface meets the solid—liquid interface. The contact angle, θ (See FIG. 8), is determined by the balance between adhesive and cohesive forces. As the tendency of a drop to spread out over a flat, solid surface increases, the contact angle decreases. Thus, the contact angle provides an inverse measure of wettability. A contact angle less than 90° (low contact angle) usually indicates that wetting of the surface is very favorable, and the fluid will spread over a large area of the surface. Contact angles greater than 90° (high contact angle) generally mean that wetting of the surface is unfavorable, so the fluid will minimize contact with the surface and form a compact liquid droplet. FIG. 9 illustrates different wettability levels based on contact angle (θ) ranges between a liquid and a surface. Example A shows a fluid on a surface with little to no wettability, example B shows a low wettability surface, while example C shows a fluid on a surface with higher wettability. Finally, example S illustrates an almost perfect wettability. Example A has a large contact angle (θ approaching or equal to 180°), B illustrates a smaller contact angle than A ($90<\theta<180°$), C has an even smaller contact angle ($0<\theta<90°$) and S represents a contact angle of essentially zero and thus a strongest liquid-to-surface interaction strength. In one embodiment, the atomizing region 11 is of high wettability providing for a liquid contact angle of less than 90 degrees which allows the device to operate independent of orientation.

The fluid barrier 17 is preferably made of a low loss electrically insulated material, preferably silicone, whose acoustic impedance is highly mismatched to the substrate material (lithium niobate and gold/titanium) and the top plate (aluminum, steel etc.) and highly matched with the fluid 7. The high mismatch of acoustic impedance between the fluid barrier 17 and both the substrate and the top plate limits energy transfer across these boundaries, while the low mismatch between the fluid barrier 17 and the fluid 7 permits energy which does enter the fluid barrier 17 to be transmitted to the fluid 7. These material boundary conditions help to effectively contain the energy of the system to the substrate 18 and the fluid 7 for atomization, despite the presence of the fluid barrier 17. The low loss characteristic of the fluid barrier 17 can be defined by an increase in power required to atomize of no more than 40%, preferably less than 15%, when the fluid barrier 17 is applied to the surface of the substrate. This characteristic is improved by minimizing the material characteristics of hysteresis, porosity, and attenuation coefficient at the operating frequency of the device, among other attributes. The low loss characteristic of the material can be defined by a low hysteresis, low porosity, and low attenuation coefficient at the operating frequency of the device, among other attributes. The benefits of being highly mismatched to the substrate are reinforced by reducing the contact area of the gasket on the substrate, in addition to the acoustic properties of the material.

The degree of mismatch, determined by the mismatch equation provided below, should be greater than 50% and as close to 100% as possible for material boundaries identified as high mismatch, and should be lower than 20% and as close to 0% as possible for material boundaries identified as low mismatch (also referred to as highly matched). The benefits of being highly mismatched to the substrate are reinforced by reducing the contact area of the gasket on the substrate, in addition to the acoustic properties of the material. This is important to ensure the impact on acoustic energy transfer of the system is minimized notwithstanding the application of the gasket. Alternate materials are possible including those that are harder, e.g., TEFLON™, but based on testing, silicone or materials with a similar durometer in the range of 20 to 90 Shore A, preferably in the range of 30 to 70 Shore A, are preferred (PDMS, Polyurethane, Polybutadiene Rubber, Neoprene, etc.).

Additionally, other parameters of importance must be managed including the compression applied to the gasket material and resulting pressure applied to the substrate. This pressure is to be optimized, in conjunction with the selection of the specific durometer (or softness) of the elastomer, its design of the gasket so as to optimize sealing at the substrate-gasket interface while minimizing any acoustic dampening. The contact area with the substrate is also to be minimized while still effectively surrounding the atomization region 11 and protecting the IDTs 19 and electrical contacts 21.

The top plate 24 which forms the supporting structure for the elastomeric gasket should be selected to sufficiently hold the elastomeric gasket and provide a stable platform against which any pre-loaded pressure is applied. This preload may be in the range of 0.25 to 3 megapascal (MPa), and preferably in the range of 0.5 to 1.5 MPa. Dimensional consistency and stiffness are important to ensure that the contact pressure and contact area are both held constant and minimize effects on acoustic performance while maintaining an effective fluid barrier 17. Preferably the top plate 24 material is such that the silicone elastomeric material is molded onto it in a secondary manufacturing step. This has advantages due to cost, by combining the fluid barrier 17 and the top plate 24 into one component as well as ensuring effective bonding, and therefore sealing, of the fluid barrier 17 material to the top plate 24. In an alternate embodiment, the elastomeric gasket may also be formed in sheets and cut to size then assembled to the top plate in a secondary operation. Top plate 24 materials can include thermoplastics, metals, thermoset plastics but most importantly materials that can readily bond to silicone and maintain a durable chemical bond in an overmold process as well as having a significantly mismatched acoustic impedance with the fluid barrier 17. The top plate 24 must also be rigid and of sufficient precision to control the position of the fluid barrier 17 as well as form an integral part of the overall package housing. The thickness of the fluid barrier 17, as defined by the distance between the top surface of the substrate and bottom surface of the top plate 24 at the thickest cross section of the fluid barrier 17, may be of importance.

Optimal gasket materials for the fluid barrier 17 are ones which have an impedance match with the fluid 7 being atomized and high mismatch with the crystal substrate 18 and top plate 24 to limit undesired energy transfer. In terms of silicone materials, the properties that may define its optimal selection for this application include the durometer or softness, tolerable temperature range, porosity, acoustic attenuation coefficient, creep resistance, surface finish, and whether it is suitable for drug contacting applications (biocompatible) and is chemically compatible with those drugs. The durometer may be in the range of 20 to 90 Shore A, preferably in the range of 30 to 70 Shore A. Tensile strength may be in the range of 200 to 1500 psi, preferably in the range of 300 to 1000 psi. The tolerable temperature range should be −65 to 400° F., and the porosity and acoustic attenuation coefficient of the material should both be minimized. The material should also resist creep well under the compressive loads and high temperatures identified over the lifespan of the device. Alternate materials that may be used include other elastomers like thermoplastic elastomers, although these materials do not usually have the same temperature tolerability or chemical resistance. Although silicone is noted above and has advantages in many areas, TEFLON™ and parylene are also contemplated as materials or coatings used for the fluid barrier.

In alternative embodiments, the fluid barrier 17 may be implemented using extremely low-density materials, such as aerogels. The density for these extremely low-density materials may be in the range from 0.0011 to 0.5 g/cm$^3$. In one implementation, the extremely low-density materials used for the fluid barrier could incorporate hydrophobic properties with a contact angle of greater than 90 degrees, and preferably greater than 110 degrees. These extremely low-density materials may increase the mismatch with the substrate and top plate, and lower system energy losses.

In yet other alternative embodiments, the fluid barrier 17 may be bonded to the substrate, either chemically or using an adhesive, to prevent fluid from entering the protected region containing the IDTs 19. Dimensional tolerance of fluid barrier placement may become easier when is applied directly to substrate 18. Additionally, use of bonding allows for assembly to the substrate 18 rather than assembly to the top plate 24. Bonding the fluid barrier to the substrate may lower or eliminate the need for applied pressure while maintaining an effective fluid seal with the substrate. In one alternative embodiment, the number of parts for the SAW nebulizer may be reduced with bonding of the fluid barrier to the substrate because a top plate 24 is not necessary if no pressure needs to be applied to the fluid barrier 17 to maintain the fluid seal with the substrate 18. Thus, rather than the embodiment of simply using applied pressure of the top plate to hold the fluid barrier against the substrate to form a seal, in alternative embodiments bonding may be used in place of any applied pressure, or both bonding and an applied pressure may be combined to achieve the desired seal between fluid barrier and substrate. Examples of chemical or adhesive bonding suitable for bonding the fluid barrier to the substrate may include overmolding of material for the fluid barrier such as LSR (liquid silicone resin) onto the substrate, melting of material to form chemical bond on substrate, and electrically insulative adhesive materials.

Acoustic Impedance is Calculated by the Following Equation:

$$\text{Acoustic Impedance} = \frac{\text{Density}}{\text{Speed of Sound}}$$

Mismatch of materials to can then be calculated to determine its compatibility.

Equation: [((Z1−Z2)/(Z1+Z2))^2], where Z1 and Z2 are the acoustic impedances of the interfacing materials. The table provided in FIG. 10 shows the calculated acoustic impedances and mismatch to gold, lithium niobate and water for a few materials.

The fluid barrier 17, being an elastomeric material and in close proximity to the atomization region 11, may also form part of the interface to both the ventilator circuit 3 and the fluid delivery system. With respect to the ventilator circuit, the atomization region 11 must be sealed to the circuit so that assurance of drug delivery to the circuit is maintained and so that no leaks are introduced to the circuit. The fluid barrier 17 preferably interfaces and seals with other elements of the atomizer 1 which are then connected to the ventilator circuit 3 through more common connections. The fluid barrier 17 contacts the surface of the substrate, which is proximal to the atomization region 11, where fluid delivery is needed. The fluid barrier 17 preferably includes a fluid delivery micro-channel 20 through which the liquid medication is delivered via the fluid delivery system to the surface of the substrate. The fluid delivery micro-channel 20 is then connected to the fluid delivery system via an interface that can also be formed out of the same elastomeric material and may form part of the same interface that also seals the atomization region 11 to the ventilator circuit 3 environment. This fluid delivery micro-channel 20 is positioned either parallel, perpendicular or vertical to the propagation of the acoustic wave with a micro-orifice 27 height in the range of 0 to 800 micrometers (μm), preferably less than 400 μm and most preferably less than 200 μm.

Alternate approaches to ensuring liquid does not migrate onto the IDTs 19 are considered and could be combined together with a fluid barrier 17 or any combination thereof. In one embodiment, a coating or some other material is applied in a thin layer on top of the substrate that has hydrophobic properties. Examples of these coatings or materials (passivation layers) deposited on the surface of the substrate 18 include $SiO_2$, TEFLON™, SiN, and other polymers. A thickness in the range of approximately 1000-3000 angstroms has been determined as optimal, although other materials could benefit from different thicknesses. This could be combined with a change in surface texture to boost the material hydrophobicity. An opposing face, not physically in contact with the substrate could contribute to fluid 7 egress away from the atomization region 11. In the case that this face is also coated with a hydrophobic passivation layer, a hydrophobic dam could be formed. This dam would operate much like a physical barrier but would not contact the substrate 18 and therefore would have potentially fewer issues with respect to impacting acoustic performance. The fluid 7 would come into contact with the hydrophobic barrier in operation and due to the surface properties at the barrier location, the fluid 7 would be sufficiently repelled and therefore contained within the atomization region 11. There are disadvantages with this design due to the possibility of other in use variables affecting how the liquid in the atomization region 11 behaves. These include orientation of the substrate with respect gravity causing the liquid to pool more heavily on one side of the substrate or another. As well, it is important to ensure that condensation from inside the humidified ventilator circuit 3 does not migrate into the device and also affect the IDTs 19. Controlling the gap height may also be difficult in practice. Both of these metallized IDT materials have different hydrophobic properties and may work in conjunction with an additional hydrophobic barrier material. Another alternate embodiment is to have a recess in the surface of the substrate, in combination with either a physical or hydrophobic barrier or on its own, which would collect and reroute the migrating liquid back to the atomization region 11. This could be a primary line of defense against fluid 7 migration or may form a safety backup in the event that the primary barriers fail. Other options would include a wicking material or other forms of directing fluid 7 in a specific way.

In an alternate embodiment, one skilled in the art can understand that the surface acoustic waves generated by SAW technology propagate throughout the substrate 18 and affect all surfaces of the substrate 18. Liquid that contacts any surface of the substrate 18, including the top surface where the IDTs 19 are located but also the sides and underside, can be atomized. Secondary atomization areas 11 can be identified which can consider location on the substrate 18 and orientation to optimize the overall performance of the SAW atomizer. In one embodiment, liquid introduced to the top side of the substrate 18 as described in earlier embodiments can be directed to facilitate flow to the side and the underside of the substrate 18. This can be accomplished by designing the fluid barrier 17 such that it prevents fluid 7 from migrating towards the IDTs 19 but allows migration towards the edge of the substrate 18 and over to the underside. The fluid barrier 17 could constrain fluid 7 to specific regions of the side and bottom of the substrate 18 if such specific areas were optimal for atomization. In an alternate embodiment, integration of the fluid barrier 17 with the fluid delivery micro channels 20 and fluid delivery system could be designed in such a way as to direct fluid 7 to atomization areas 11 on both the top, side and bottom surfaces of the substrate. Fluid delivery micro channels 20 could originate from the interface at the top surface of the substrate and direct fluid 7 to the side and bottom surfaces with unique fluid delivery orifices 27 delivering fluid 7 to the surface of the substrate 18 in various unique locations.

Alternately, a duplication approach could be taken whereby the fluid delivery system has two interfaces. In this embodiment, there would be fluid delivery interfaces between the top surface and the bottom surface. One skilled in the art can appreciate that to integrate these elements a unique packaging design considering the top plate 24 and PCB 25 would be optimized to ensure earlier described variables that are deemed important to ensure effective fluid barrier 17 function and atomization are maintained. For instance, maintaining the same material properties of the fluid barrier 17 as well as the precise location and contact between the fluid barrier 17 and the substrate 18. This would be required whether contacting the top, side or bottom of the substrate 18 to minimize any impact to atomization while also ensuring effective prevention of fluid migration to the IDTs 19. As the IDTs 19 are typically located on only one surface of the substrate 18, fluid migration and therefore the function of the fluid barrier 17 on the side and bottom surfaces would be more focused on containing fluid 7 to optimize atomization rather than protecting the IDTs 19. However, as fluid can wick and, through capillary action, migrate across multiple surfaces, the fluid barrier 17 would have some element of IDT 19 protection functionality on all surfaces.

In one alternative embodiment, as shown in FIGS. 11-14, the atomization engine 12A of the SAW nebulizer may include a mechanism for containing the medication to be nebulized in the atomization region 11. In this alternative embodiment, an active switch system may be used to detect the migration of fluid towards the IDTs 19. The switch described in this embodiment may comprise an open circuit which is completed by the presence of a conductive fluid. This active switch system may include sensing electrodes (30-33) that are either metallized directly on the substrate surface or removably attached within the atomizer engine to determine the position of the fluid. The active switch system may then adjust the incoming electrical signal to the substrate 18, based on the fluid position sensed via the electrodes, to reposition the fluid towards the center of the atomization region 11. A positive electrical contact 30, 32 and a negative electrical contact 31,33 would be positioned so that when fluid contacts both the positive and negative contacts it closes the circuit. A set of contacts may be located on both the left side 30,31 and the right side 32,33 of the atomization region 11. The left-side and right-side circuits may be separate and when closed would indicate which side the fluid is on. In the illustrated implementation of FIGS. 11-14, there is no physical contact of the fluid barrier 17 with the substrate and a minimum clearance 34 is maintained between the substrate 18 and the fluid barrier 17. The embodiment of FIGS. 11-14 would be suitable for applications using conductive medication/fluids 7. For example, saline solutions are good conductors. Other salts and inorganic chemicals dissolved in water, or ionic solutions with electrically charged particles able to conduct electrical current, would also be candidates for use with the embodiment of FIGS. 11-14. The fluid position on the atomization region 11, based on the sensed position according to the electrodes, may be adjusted by varying the frequency of the SAW nebulizer, for example through shifts in frequency of 0.2% of the operating frequency of the device, to move the fluid towards to center of the atomization region 11 until the fluid no longer contacts both positive and negative electrical contacts causing the switch to be deactivated. This adjustment and preferred resulting positioning of the fluid is best illustrated in FIGS. 12A-12C (sectional top view) and FIGS. 14A-14C (sectional side view), where the fluid is shown out of center to the left (FIGS. 12A, 14A) and in contact with the electrodes 30,31 on one side, or out of center to the other side of the atomization region 11 (FIGS. 12C, 14C) and in contact with electrodes 32,33 on the other side, and after adjusting the frequency of the device to move the fluid to the center in response to detecting the closed circuit of the fluid contacting one or the other sets of electrodes, the desired resulting position of the fluid 7 in the atomization region 11 (FIGS. 12B, 14B) after the frequency adjustments have been made.

Although shown in FIGS. 11-14 with a gap 34 between fluid barrier 17 and substrate 18, and usable without a physical barrier as shown in prior embodiments, the atomization engine 12A of FIGS. 11-14 may be modified in an alternative embodiment to combine a physical barrier, such as a fluid barrier pressed against and/or bonded to the substrate as discussed above, with the electrical detection circuit and fluid steering discussed in this embodiment to bolster reliability in keeping the fluid away from the IDTs 19.

Figure 15:
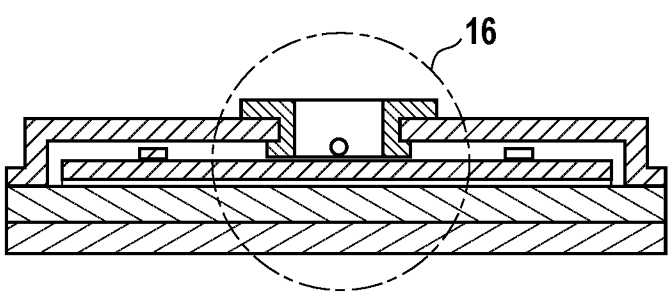
FIG. 15 is a side sectional view of a second alternative embodiment of the atomizer engine of FIGS. 6A-6C.
Figure 16:
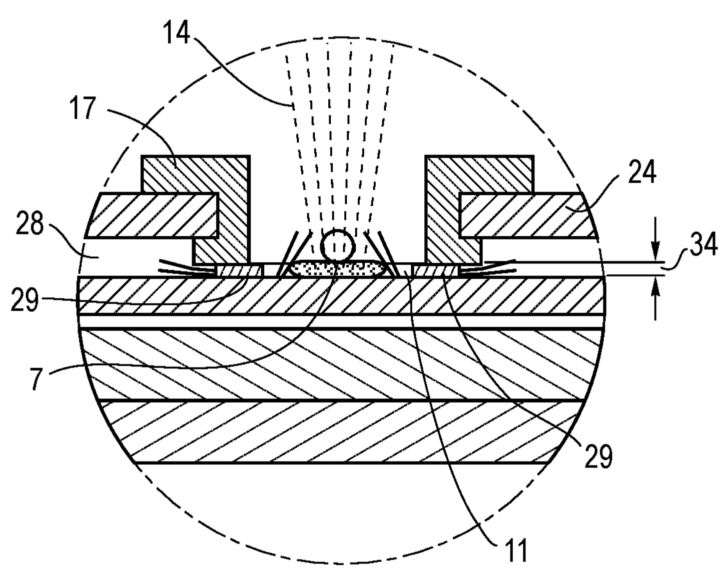
FIG. 16 is a sectional view of the atomizer engine of FIG. 15.

FIGS. 15-16 illustrate another alternative embodiment of the atomization engine 12B where the fluid 7 is contained to the atomization region 11 using air flow 29. This air flow 29 can be directed through the atomizer engine and into the ventilator circuit from an external source, or the flow could be directed perpendicular to the atomization region 11 and circulated within the atomizer engine. The air flow for this embodiment may originate from either an external wall air source typically available in a medical office or hospital room, or from an integrated compressor in the controller. The rate of the air flow 29 supplied should be great enough to create a positive pressure within the body of the device (air cavity 28) to repel the fluid with the required magnitude of pressure to keep the fluid from leaking out of the atomization region under the non-fluid barrier 17. The desired rate for the air flow 29 may be selected based on the application in which the device would be used (ventilator vs. spontaneous breathing, etc.) as well as the dimension of flow channel opening used to direct the positive pressure towards the atomization region 11.

As with the version of the atomizer engine illustrated in FIGS. 11-14 that used an electrical sensor to detect fluid position and then adjusted the acoustic frequency generated and applied by the IDTs to adjust the position of the fluid in the atomizing region, the embodiment of FIGS. 15-16 also may include a minimum clearance 34 between the fluid barrier 17 and the substrate 18 such that there is no physical contact of the fluid barrier with the substrate. In one embodiment, the non-contact fluid barrier 17 is preferably positioned as close to the surface of the substrate 18 as possible within manufacturing tolerances while maintaining a minimum clearance 34. Additionally, the fluid barrier 17 may be provided with additional hydrophobic properties to improve reliability in protecting the IDTs 19 in one implementation.

The invention claimed is:

1. A surface acoustic wave atomizer system for use in atomizing a medicament for patient delivery, the surface acoustic wave atomizer system comprising:

an atomizer engine comprising:

a piezoelectric substrate;

- at least one set of interdigitated transducers (IDTs) positioned on a first side of the piezoelectric substrate;
- an atomization region positioned on the first side of the piezoelectric substrate adjacent to the at least one set of IDTs;
- a top plate positioned over the first side of the piezoelectric substrate and enclosing a portion of the piezoelectric substrate other than the atomization region, such that the at least one set of IDTs are enclosed under the top plate, the top plate comprising a rigid material and being spaced from the first side of the piezoelectric substrate to define an air gap above the IDTs; and
- a fluid barrier surrounding the atomization region on the piezoelectric substrate and forming a seal against the piezoelectric substrate and the top plate, wherein the fluid barrier is positioned to prevent liquid in the atomization region from coming into contact with the IDTs on the first side of the piezoelectric substrate;

wherein the fluid barrier comprises an elastomer having a Shore A durometer between 30 and 70, and is comprised of a material having an acoustic impedance that is highly mismatched to both the piezoelectric substrate and to the top plate, an acoustic mismatch between the fluid barrier and each of the piezoelectric substrate and the top plate being greater than 50%.

2. The surface acoustic wave atomizer system of claim 1, wherein the fluid barrier comprises an electrically insulated material which exhibits low acoustic energy losses at an operating frequency of the piezoelectric substrate.

3. The surface acoustic wave atomizer system of claim 1, wherein the fluid barrier is removably attached to the first side of the piezoelectric substrate.

4. The surface acoustic wave atomizer system of claim 1, wherein the fluid barrier is configured to have a micro channel formed in a wall of the fluid barrier, the micro channel configured to have a first opening adjacent to the atomization region on the first side of the piezoelectric substrate and a second opening wherein a liquid supply is connected.

5. The surface acoustic wave atomizer system of claim 4, wherein the atomizer engine further comprises:

a base configured to have a first side bonded to the piezoelectric substrate via an electrically insulating bonding layer; and a circuit board, wherein a second side of the base opposite the first side of the base is mounted to the circuit board, and wherein the circuit board is configured to deliver electrical signals received from a controller to the piezoelectric substrate via electrical contacts formed between the circuit board and the at least one set of IDTs.

6. The surface acoustic wave atomizer system of claim 1, further comprising a gas pathway fitting having a first end and a second end, the first end attached to the atomizer engine and positioned to receive an atomized fluid from the atomization region, and the second end attachable to a patient delivery interface.

7. The surface acoustic wave atomizer system of claim 6, wherein the surface acoustic wave atomizer system is positioned in a ventilator circuit and the patient delivery interface is a ventilator adapter for directing the atomized fluid from the atomizer engine into the ventilator circuit.

8. The surface acoustic wave atomizer system of claim 6, wherein the surface acoustic wave atomizer system is part of a handheld system and the patient delivery interface is one of a mouthpiece or a mask configured to direct the atomized fluid from the atomizer engine to a patient.

9. The surface acoustic wave atomizer system of claim 1, wherein the elastomer is selected from the group consisting of silicone, PDMS, polyurethane, polybutadiene rubber, and neoprene.

10. The surface acoustic wave atomizer system of claim 1, wherein the elastomer comprises silicone.

11. A surface acoustic wave atomizer system for atomizing a liquid medicament for patient delivery, the surface acoustic wave atomizer system comprising:

a piezoelectric substrate having a side with at least one interdigitated transducer and an atomization region separate from the at least one interdigitated transducer;

a top plate spaced away from the side of the piezoelectric substrate and enclosing the side of the piezoelectric substrate other than the atomization region, wherein the piezoelectric substrate is captured between the top plate and a base;

a fluid barrier attached to the top plate and surrounding the atomization region on the piezoelectric substrate, the fluid barrier defining an atomization path from the atomization region through the top plate and separating the at least one interdigitated transducer from the atomization region;

a fluid supply channel extending through a wall of the fluid barrier from a first fluid channel opening in a portion of the fluid barrier outside of the top plate to a fluid orifice in the fluid barrier oriented toward the atomizing region and between an outside of the top plate and the side of the piezoelectric substrate; and wherein the fluid barrier is formed of a material having an acoustic impedance that is highly mismatched with both the piezoelectric substrate and the top plate, an acoustic mismatch between the fluid barrier and each of the piezoelectric substrate and the top plate being greater than 50%, and having an acoustic impedance that is highly acoustically matched to the liquid medicament.

12. The surface acoustic wave atomizer system of claim 11, wherein the fluid barrier forms a seal against the piezoelectric substrate by compression of the fluid barrier between the top plate and piezoelectric substrate to form a seal against the piezoelectric substrate and configured to prevent liquid medicament in the atomizing region from contacting the at least one interdigitated transducer.

13. The surface acoustic wave atomizer system of claim 11, wherein the fluid barrier is maintained above the piezoelectric substrate by the top plate without physically contacting the piezoelectric substrate, the fluid barrier further comprises a hydrophobic material, and wherein the atomizing region comprises a region of high wettability.

14. The surface acoustic wave atomizer system of claim 13, further comprising a fluid sensor positioned at an edge of the atomizing region and inside the fluid barrier, the fluid sensor configured to sense a position of the liquid medicament within a portion of the piezoelectric substrate and adjust an incoming signal to the piezoelectric substrate to change a frequency generated by the at least one interdigitated transducer to adjust a position of the liquid medicament in the atomization region.

15. The surface acoustic wave atomizer system of claim 11, wherein the fluid barrier is formed of a material selected from the group consisting of silicone, PDMS, polyurethane, polybutadiene rubber, and neoprene.

16. The surface acoustic wave atomizer system of claim 11, wherein the fluid barrier is formed of silicone.

* * * * *